US007572274B2

(12) United States Patent
Yassinzadeh

(10) Patent No.: US 7,572,274 B2
(45) Date of Patent: Aug. 11, 2009

(54) SELF-TENSIONING VASCULAR OCCLUSION DEVICE AND METHOD FOR ITS USE

(75) Inventor: Zia Yassinzadeh, San Jose, CA (US)

(73) Assignee: Cardiva Medical, Inc., Mountain View, CA (US)

( * ) Notice: Subject to any disclaimer, the term of this patent is extended or adjusted under 35 U.S.C. 154(b) by 526 days.

(21) Appl. No.: 10/857,177

(22) Filed: May 27, 2004

(65) Prior Publication Data

US 2005/0277980 A1 Dec. 15, 2005

(51) Int. Cl.
*A61B 17/08* (2006.01)
*A61M 29/00* (2006.01)
*A61M 31/00* (2006.01)

(52) U.S. Cl. ........................ 606/213; 606/191; 606/198

(58) Field of Classification Search ................. 606/111, 606/213, 191, 198, 200, 192, 194; 604/93.01-96.01
See application file for complete search history.

(56) References Cited

U.S. PATENT DOCUMENTS 4,744,364 A 5/1988 Kensey
4,850,975 A 7/1989 Furukawa
4,852,568 A 8/1989 Kensey
4,890,612 A 1/1990 Kensey
5,061,274 A 10/1991 Kensey
5,108,420 A 4/1992 Marks
5,108,421 A 4/1992 Fowler
5,171,259 A 12/1992 Inoue
5,197,971 A 3/1993 Bonutti
5,258,000 A 11/1993 Gianturco
5,290,552 A 3/1994 Sierra et al.
5,292,332 A 3/1994 Lee
5,383,896 A 1/1995 Gershony et al.

(Continued)

FOREIGN PATENT DOCUMENTS

WO WO 92/22252 12/1992

(Continued)

OTHER PUBLICATIONS

U.S. Appl. No. 10/718,504, filed Nov. 19, 2003.

(Continued)

*Primary Examiner*—Anhtuan T Nguyen
*Assistant Examiner*—Amy T Lang
(74) *Attorney, Agent, or Firm*—Townsend and Townsend and Crew, LLP

(57) ABSTRACT

The present invention advantageously provides self-tensioning occlusion devices, systems, and methods for percutaneous access and closure of vascular puncture sites. One device comprises a catheter body having a proximal end and a distal end, an occlusion member, and a tensioning member. The occlusion member, such an expansible member, is disposed on a distal end of the body. The tensioning member, such as a spring or coil, is slidably disposed over the body and proximal the expansion member. Generally, during application, the tensioning member will be positionable against subcutaneous tissue so as to lodge and anchor the expansible member against the puncture site. In particular, the expansible member allows for sealing of the puncture site while the tensioning member applies and maintains tension to the expansible occluder so that it is seated against the puncture site at a vascular surface.

14 Claims, 7 Drawing Sheets

U.S. PATENT DOCUMENTS

| | | | | |
|---|---|---|---|---|
| 5,419,765 | A | 5/1995 | Weldon et al. | |
| 5,437,631 | A | 8/1995 | Janzen | |
| 5,454,833 | A | 10/1995 | Boussignac et al. | |
| 5,456,667 | A | 10/1995 | Ham et al. | |
| 5,486,195 | A | 1/1996 | Myers et al. | |
| 5,507,744 | A | 4/1996 | Tay et al. | |
| 5,626,601 | A | 5/1997 | Gershony et al. | |
| 5,630,833 | A | 5/1997 | Katsaros et al. | |
| 5,634,936 | A | 6/1997 | Linden et al. | |
| 5,728,134 | A | 3/1998 | Barak | |
| 5,782,860 | A | 7/1998 | Epstein et al. | |
| 5,810,810 | A | 9/1998 | Tay et al. | |
| 5,836,913 | A | 11/1998 | Orth et al. | |
| 5,851,210 | A | 12/1998 | Torossian | |
| 5,861,003 | A | 1/1999 | Latson et al. | |
| 5,868,778 | A | 2/1999 | Gershony et al. | |
| 5,895,398 | A | 4/1999 | Wensel et al. | |
| 5,922,009 | A | 7/1999 | Epstein et al. | |
| 5,951,583 | A | 9/1999 | Jensen et al. | |
| 5,951,589 | A | 9/1999 | Epstein et al. | |
| 5,957,952 | A | 9/1999 | Gershony et al. | |
| 6,012,457 | A | 1/2000 | Lesh | |
| 6,017,359 | A | 1/2000 | Gershony et al. | |
| 6,048,358 | A | 4/2000 | Barak | |
| 6,056,769 | A | 5/2000 | Epstein et al. | |
| 6,056,770 | A | 5/2000 | Epstein et al. | |
| 6,080,182 | A | 6/2000 | Shaw et al. | |
| 6,146,396 | A | 11/2000 | Kónya et al. | |
| 6,179,860 | B1 * | 1/2001 | Fulton et al. | 606/200 |
| 6,213,988 | B1 * | 4/2001 | McIvor et al. | 604/264 |
| 6,248,124 | B1 | 6/2001 | Pedros et al. | |
| 6,296,657 | B1 | 10/2001 | Brucker | |
| 6,464,712 | B1 * | 10/2002 | Epstein et al. | 606/213 |
| 6,656,207 | B2 | 12/2003 | Epstein et al. | |
| 6,913,614 | B2 | 7/2005 | Marino et al. | |
| 6,994,689 | B1 * | 2/2006 | Zadno-Azizi et al. | 604/107 |
| 7,025,776 | B1 | 4/2006 | Houser et al. | |
| 7,115,127 | B2 | 10/2006 | Lindenbaum et al. | |
| 7,220,246 | B2 * | 5/2007 | Raulerson et al. | 604/174 |
| 7,223,266 | B2 | 5/2007 | Lindenbaum et al. | |
| 2001/0034537 | A1 * | 10/2001 | Shaw et al. | 606/213 |
| 2002/0065536 | A1 * | 5/2002 | Hart et al. | 606/232 |
| 2002/0072767 | A1 | 6/2002 | Zhu | |
| 2002/0072768 | A1 * | 6/2002 | Ginn | 606/213 |
| 2002/0133123 | A1 | 9/2002 | Zucker | |
| 2003/0055454 | A1 | 3/2003 | Zucker | |
| 2003/0120291 | A1 | 6/2003 | Chin et al. | |
| 2003/0176875 | A1 | 9/2003 | Anderson et al. | |
| 2003/0191493 | A1 | 10/2003 | Epstein et al. | |
| 2003/0225420 | A1 * | 12/2003 | Wardle | 606/151 |
| 2004/0176798 | A1 | 9/2004 | Epstein et al. | |
| 2005/0038453 | A1 | 2/2005 | Raulerson | |

FOREIGN PATENT DOCUMENTS

| | | |
|---|---|---|
| WO | WO 95/05121 | 2/1995 |
| WO | WO 96/24290 | 8/1996 |
| WO | WO 98/34546 | 8/1998 |
| WO | WO 98/40017 | 9/1998 |
| WO | WO 00/06029 | 2/2000 |
| WO | WO 00/06031 | 2/2000 |

OTHER PUBLICATIONS

U.S. Appl. No. 10/821,633, filed Apr. 9, 2004.
Datascope Corporation; "VasoSeal" product brochure; 1991.
Sherwood, Davies & Geck; "AngioSeal" product brochure; 1977.

* cited by examiner

SELF-TENSIONING VASCULAR OCCLUSION DEVICE AND METHOD FOR ITS USE

BACKGROUND OF THE INVENTION

1. Field of the Invention

The present invention relates generally to devices, systems, and methods for percutaneous sealing of puncture sites in body lumens or tissue tracts. More specifically, the present invention relates to self-tensioning vascular occlusion devices, systems, and methods for its use for hemostasis of vascular puncture sites.

Percutaneous access of blood vessels in the human body is routinely performed for diagnostics or interventional procedures such as coronary and peripheral angiography, angioplasty, atherectomies, placement of vascular stents, coronary retroperfusion and retroinfusion, cerebral angiograms, treatment of strokes, cerebral aneurysms, and the like. Patients undergoing these procedures are often treated with anti-coagulants such as heparin, thrombolytics, and the like, which make the closure and hemostasis process of the puncture site in the vessel wall at the completion of such interventional procedures more difficult to achieve.

Various devices have been introduced to provide hemostasis, however none have been entirely successful. Some devices utilize collagen or other biological plugs to seal the puncture site. Alternatively, sutures and/or staples have also been applied to close the puncture site. External foreign objects such as plugs, sutures, or staples however may cause tissue reaction, inflammation, and/or infection as they all "leave something behind" to achieve hemostasis.

There is also another class of devices that use the body's own natural mechanism to achieve hemostasis wherein no foreign objects are left behind. Such devices typically provide hemostasis by sealing the puncture site from the inside of the vessel wall wherein the device is left in place in the vessel lumen until hemostasis is reached and thereafter removed. These devices generally comprises two separate and distinct components, namely a catheter and an external tensioning element. The external tensioning element is typically connected to the catheter shaft and rests on an exterior surface of the skin after the catheter is positioned in the vessel. It provides tension to the catheter at the puncture site as well as anchors the applied tension so that a tip of the deployed catheter is maintained against the vessel wall at the puncture site. The external tensioning element is kept in tension for a period of time.

Although such devices have achieved relative levels of success, the external tensioning element is not always easy and convenient in its application. Further, the external tensioning element may not always preserve the integrity of the catheter system. For example, manipulation of the catheter when the external tensioner is applied or removed may cause disruption of the seal at the vessel puncture site, resulting in bleeding or hematoma formation (i.e., leaking of blood into interstitial space). Also, the external tensioner may be subject to being dislodged accidentally while in use, which may result in complications, such as resumption of bleeding.

In light of the above, it would be desirable to provide alternative devices, systems, and methods for complete hemostasis of a puncture site in a body lumen, particularly blood vessels of the human body. It would be particularly desirable if such devices, systems, and methods utilize the body's own natural healing mechanism to achieve hemostasis. It would be further desirable if such devices and systems utilize a simple construction and user interface allowing for convenient application without numerous intermediary steps. Further, such devices should be reliable, preserve the integrity of the system, and provide for appropriate tension application without the need for user intervention. At least some of the these objective will be met by the devices, systems, and methods of the present invention described hereinafter.

2. Description of the Background Art

Hemostasis devices for use in blood vessels and tracts in the body are described in co-pending U.S. patent application Ser. Nos. 10/821,633 and 10/718,504 and U.S. Pat. Nos. 6,656,207; 6,464,712; 6,056,770; 6,056,769; 5,922,009; and 5,782,860, assigned to the assignee of the present application. The following U.S. Patents and Publications may be relevant to the present invention: U.S. Pat. Nos. 4,744,364; 4,852,568; 4,890,612; 5,108,421; 5,171,259; 5,258,000; 5,383,896; 5,419,765; 5,454,833; 5,626,601; 5,630,833; 5,634,936; 5,728,134; 5,836,913; 5,861,003; 5,868,778; 5,951,583; 5,957,952; 6,017,359; 6,048,358; 6,296,657; U.S. Publication Nos. 2002/0133123; 2003/0055454; and 2003/0120291.

The full disclosures of each of the above mentioned references are incorporated herein by reference.

BRIEF SUMMARY OF THE INVENTION

The present invention advantageously provides self-tensioning occlusion devices, systems, and methods for percutaneous access and closure of puncture sites in a body lumen, particularly blood vessels of the human body. It will be appreciated however that application of the present invention is not limited to the blood vasculature, and as such may be applied to any of the vessels, even severely tortuous vessels, ducts, and cavities found in the body as well as tissue tracts. Such closure devices, systems, and methods utilize the body's own natural healing mechanism to achieve complete hemostasis without leaving any foreign objects behind.

In a first aspect of the present invention, a device for hemostasis of a puncture site in a body lumen or tissue tract comprises a catheter body having a proximal end and a distal end, an occlusion member, and a tensioning member. The occlusion member, such as an expansible member, is disposed on a distal end of the body. The tensioning member is slidably disposed over the body and proximal the expansion member. Generally, during application, the tensioning member will be positionable against subcutaneous tissue so as to lodge and anchor the expansible member against the puncture site. In particular, the expansible member allows for sealing of the puncture site while the tensioning member applies and maintains tension to the expansible occluder so that it is seated against the puncture site at a vascular surface (e.g., blood vessel wall).

The present invention integrates the expansible occluder with the tensioning member to form a single unitary catheter construction. This simple construction and user interface allows for easy and convenient application of the device without numerous intermediary steps. Further, the tensioning member is not subject to interference due to catheter integration. This results in a more reliable, safe, and effective device which preserves the integrity of the system, which in turn reduces the risk of bleeding, hematoma formation, thrombosis, embolization, and/or infection, particularly in lengthy applications.

The tensioning member typically comprises a spring or coil of wire formed from a variety of medical grade materials including stainless steel, shape memory alloy, superelastic metal, and the like. The wire may have a diameter in a range from about 0.02 mm to about 1 mm and form any number of loops, typically from 1 to 30 loops. The spring or coil diameter will be in a range from about 1 mm to about 10 mm in a relaxed state. As discussed in more detail below, the relaxed spring diameter is sufficiently large to allow it to be slidably received over the catheter body and greater than an inner diameter of a delivery sheath. A tubular member may additionally be slidably disposed over the catheter body and coupleable to a proximal end of the tensioning member. Such a tubular member may aid in loading and removal of the tensioning element as well as provide a mechanism for applying a predetermined amount or additional tension upon the expansible member.

The expansible member may comprise a variety of structures including a braided filament, mesh layer, spring, coil, slotted tube, or balloon. Generally, a deformable membrane will at least be partially disposed over the expansible member. However, in the case where the expansible member comprises a braided mesh, the braid may be sufficiently tight without the use of a membrane so that in a deployed state it can adequately occlude the puncture site in the vessel. The expansible member may also be coated with a highly hydrophobic coating such as TEFLON® or HYDRO-SIL®. The combination of small pores in the braided mesh and high surface tension of the expansible member achieved by the use of such coatings may provide adequate barrier to blood flow through the puncture site. Exemplary expansible member structures are described in detail in co-pending U.S. patent application Ser. No. 10/718,504, assigned to the assignee of the present application and incorporated herein by reference. The expansible member occludes the vascular surface at the puncture site without substantially disturbing the blood flow to the lower extremities. In some embodiments, the deformable membrane may further comprise a membrane tip at the most distal end of the catheter body so as to provide a soft and blunt point for percutaneous access. In other embodiments, a flexible tip deflector may be coupleable to the catheter body distal the expansible member so as to prevent any damage to the surrounding vessel wall.

The device of the present invention further comprises deployment means, such as a two part handle assembly, coupleable to the proximal end of the catheter body. A locking or latching mechanism may be incorporated into the two part handle so as to securely and reliably lock the expansible member in an expanded configuration. Further, such a locking or latching mechanism may also be incorporated into the tubular member of the tensioning element so as to provide a connection to the deployment means for easy loading into the sheath and removal of the tensioning element and the catheter from the body.

In another aspect of the present invention, methods to use the device for hemostasis of a puncture site in a blood vessel at an end of a tissue tract are provided. A catheter having a proximal end, a distal end, an expansible member at the distal end thereof, and a tensioning member proximal the expansible member is provided. The catheter is inserted through an opening in a skin surface, typically through a seal of an existing sheath, so as to traverse a length of the sheath and expose the expansible member of the catheter in a lumen of the blood vessel. The expansible member of the catheter is then deployed in the blood vessel. The sheath is then slowly pulled out of the body, placing the expansible member of the catheter against the inner wall of the vessel at the puncture site. As the sheath is further removed, the tensioning member of the catheter which is slidably located on the catheter shaft is released from the sheath and into the fascia surrounding the tissue track. The tensioning member is lodged against the fascia, providing for adequate tension on the expansible member to seal the puncture site.

Hence, the expansible occluder of the device may be set by the removal of the sheath, therefore simplifying the procedure. Further, the tensioner may be set by the removal of the sheath so as to provide for appropriate tension application. This may be achieved by the interference between the sheath and the tensioning coil as a result of the coil diameter, in a relaxed state, being larger than the sheath diameter. In other embodiments, the device may be equipped with a loading element, a flexible elongated tube that contains the tensioning element and can be slidably received within the sheath. In such an embodiment, the tension is set by the interference between the tensioning coil and the loader as the sheath and the loader are removed. When a loader is used, the tension produced and exerted on the expansible member remains the same. The use of the loader or the sheath to set the tension advantageously eliminates user involvement in setting the tension, and consequently provides for more precise and consistent application of tension. As such, the devices of the present invention do not require measurements, such as length measurements for the placement of the expansible member or force measurements for application of tension. Further, removal of the catheter is simplified, as there is no external tensioner to be removed. Generally, the integrated design of the present invention greatly simplifies and automates operation of the device without any intermediary steps between its application and removal.

Typically, the amount of tension applied to the expansible member is in a range from about 0.5 ounce to 30 ounces, preferably in a range from about 5 ounces to 15 ounces. The expansible member is further anchored against the puncture site. This is typically carried out by the tensioning member. However, in some embodiments, an external clip seated against the skin surface may be utilized to anchor and/or provide additional tension upon the expansible member. Still further, tension on the expansible member may be increased by pulling on the tubular member coupled to the tensioning spring in a proximal direction. It will be appreciated that a predetermined amount of tension may be applied to the expansible member. For example, the tubular member coupled to the tensioning spring may be displaced a predetermined distance to effect a predetermined transitional tension onto the expansible member.

Deployment of the expansible member typically comprises pushing or pulling a two part handle assembly coupled to the expansible member. The parts of the handle assembly are locked by conventional mechanical means, so that the expansible member securely remains in a deployed configuration. Methods of the present invention may further comprise interlocking the handle assembly with the tubular member coupled to the tensioning spring. As discussed above, this connection provides for easy loading and removal of the tensioning element and/or for re-introducing the sheath over the catheter if necessary. Generally, the expansible member is deployed to an expanded configuration within the blood vessel having a diameter in a range from about 3 mm to about 10 mm.

The expansible member and tensioning member are deployed sequentially or simultaneously. Deployment of the tensioning member may comprise of removing an elongated tubular member, such as a delivery sheath or loading element, disposed over the tensioning member in a proximal direction. The loading element is preferably removed concurrently with the sheath. In particular, the diameter of the tensioning member in a relaxed state is greater than the inner diameter of the delivery member so as to provide adequate positioning and tension upon the expansible member.

The present invention further includes kits comprising a self-tensioning vascular occlusion device as described herein and instructions to use the device for hemostasis of a puncture site in a blood vessel. Instructions for use will generally recite the steps for performing one or more of the above described methods. The instructions will often be printed, optionally being at least in part disposed on packaging. The instructions may alternatively comprise a videotape, a CD-ROM or other machine readable code, a graphical representation, or the like showing any of the above described methods. The kit may further include additional components of the system, such as a loading element, sheath, external clip, or the like. The kit components will be packaged in a conventional medical device package that is usually sterile, such as a pouch, tray, box, or the like.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

DETAILED DESCRIPTION OF THE INVENTION

Figure 1:
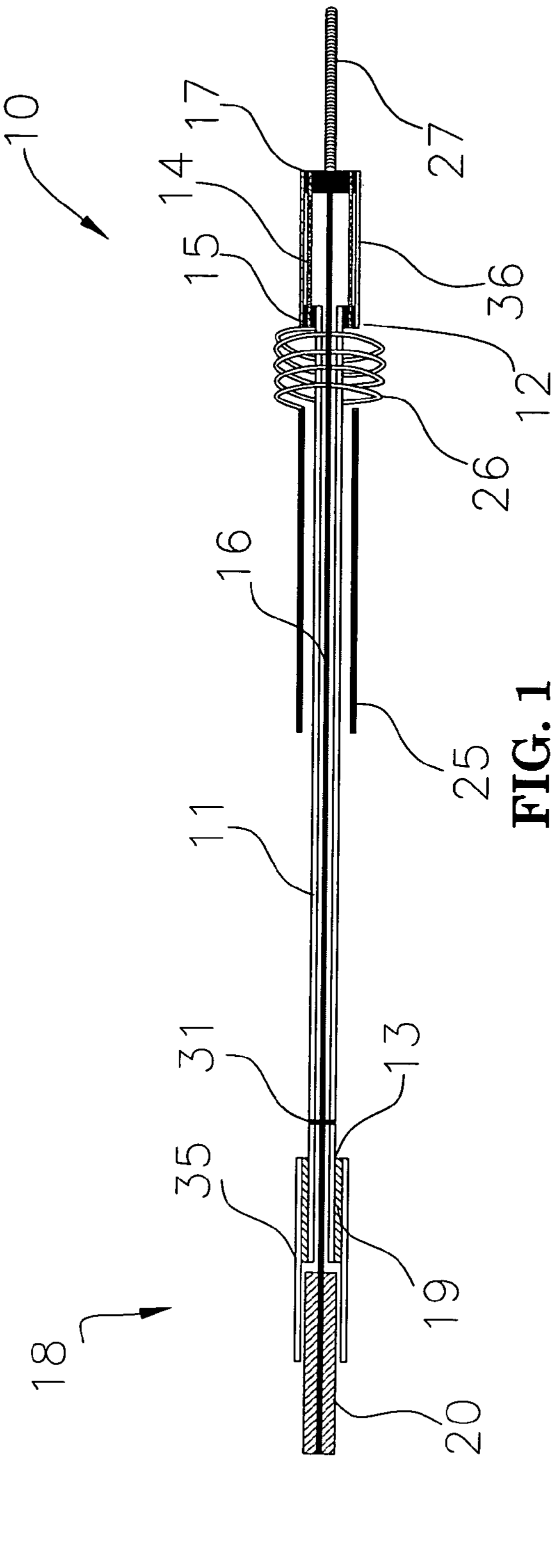
FIG. 1 illustrates an exemplary self-tensioning vascular occlusion device for hemostasis of vascular puncture sites constructed in accordance with the principles of the present invention.

Referring now to FIG. 1, an exemplary self-tensioning vascular occlusion device 10 for hemostasis of vascular puncture sites constructed in accordance with the principles of the present invention is illustrated. Device 10 comprises a first flexible elongated tubular member 11 having a distal end 12 and a proximal end 13. Tubular member 11 may be formed from coiled stainless steel tubing or polymer materials such as nylon, polyurethane, polyimide, PEEK®, PEBAX®, and the like. Tubular member 11 may have a length in a range from about 10 cm to about 50 cm, preferably in the range from about 15 cm to about 30 cm and a diameter in the range from about 0.25 mm to about 5 mm, preferably in the range from about 0.5 mm to about 2 mm. An expansible occlusion member 14 is disposed on the distal end 12 of tubular member 11. Further, a tensioning member 26 is slidably disposed over the tubular member 11 and proximal the expansible member 14. It will be appreciated that the above depictions are for illustrative purposes only and do not necessarily reflect the actual shape, size, or dimensions of the device 10. This applies to all depictions hereinafter.

Figure 2:
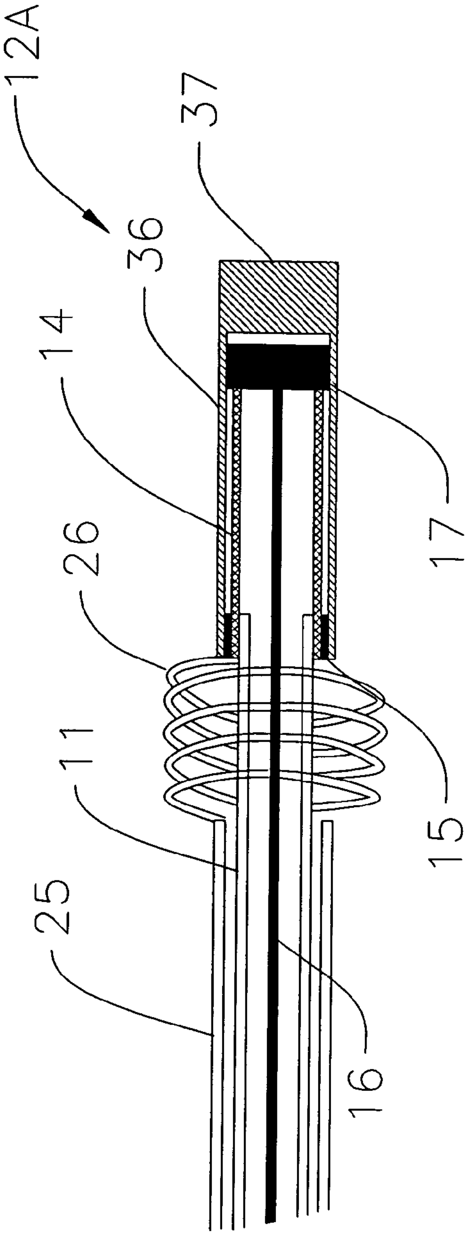
FIG. 2 illustrates an alternative embodiment of the occlusion membrane that may be employed in any of the devices disclosed herein.

Referring now to FIG. 2, the expansible member 14 may at least partially or preferably be fully covered with an elastomeric membrane material 36. Membrane 36 may be formed from a variety of medical grade materials, such as thermoplastic elastomers (e.g., CHRONOPRENE® or POLYBLEND®) having durometers in a range from 15 Å to about 40 Å. Membrane 36 may be connected at a distal connection point 17 and a proximal connection point 15. Adhesives such as LOCTITE® 4014 may be used to attach membrane 36 to the catheter 11. Alternatively, membrane 36 may take a form of a sock having its distal end sealed through a heat stake process or the like. In this case membrane 36 may not have to be attached distally. Membrane 36 preferably has a diameter that is sufficient to cover the expansible member 14. In some embodiments, membrane 36 may be designed and attached to facilitate expansible member 14 deployment as well as to reduce the amount of required elongation when the expansible member 14 is deployed. This may be achieved by molding the membrane 36 so that its midpoint diameter, where deployed expansible member 14 has its greatest diameter, is larger than its proximal and distal end diameters (e.g., a spherical shape). Membrane 36 may also be formed like a tube with a larger diameter than needed (diameter of retracted expansible member 14), and then stretched over expansible member 14 and attached. The stretch should be enough to reduce the diameter of the membrane 36 to that of the expansible member 14. In such a case, when member 14 is deployed, there is less elongation and stress experienced by membrane 36. The membrane 36 may additionally form a membrane tip 37 at a distal end 12A of the catheter 11 so as to provide a soft and blunt point for percutaneous access.

Figures 3A, 3B, 4A, 4B:
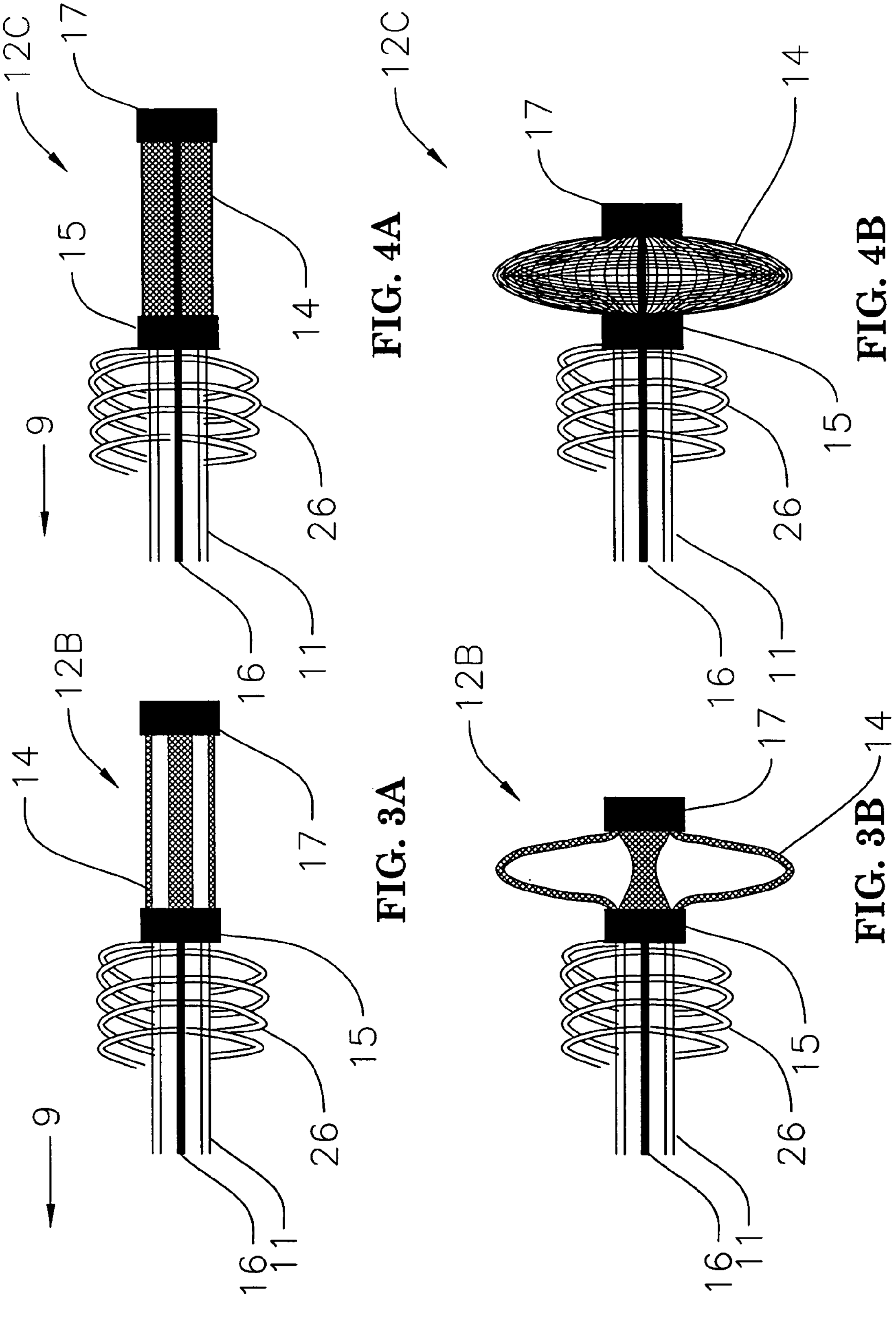
FIGS. 3A and 3B illustrate another embodiment of the expansible member in a retracted configuration and an expanded configuration respectively that may be employed in any of the devices disclosed herein.
FIGS. 4A and 4B illustrate yet another embodiment of the expansible member in a retracted configuration and an expanded configuration respectively that may be employed in any of the devices disclosed herein.

Referring now to FIGS. 3A, 3B, 4A, and 4B, expansible member 14 may be formed from a variety of medical grade materials, including stainless steel, superelastic material such as NITINOL®, or polymer materials such as nylon, polyurethane, polyimide, PEEK®, PEBAX®, and the like. The expansible member 14 in a retracted or collapsed state has a diameter of less than about 3 mm, preferably less than about 1.5 mm, as shown in FIGS. 3A and 4A. When deployed, the expansible member 14 in an expanded state has a diameter in a range from about 3 mm to about 10 mm, preferably from about 4 mm to about 7 mm, as shown in FIGS. 3B and 4B. The expansible member 14 may comprise a push or a pull type deployment means as is described in detail co-pending U.S. patent application Ser. No. 10/821,633, assigned to the assignee of the present application and incorporated herein by reference. Exemplary expansible member structures 14 are described in detail in co-pending U.S. patent application Ser. No. 10/718,504, assigned to the assignee of the present application and incorporated herein by reference. Still further embodiments of a braided mesh member 14 are disclosed in U.S. Pat. No. 5,836,913, also incorporated herein by reference.

In a preferred embodiment, the expansible member 14 comprises a pull type, where the retracted state of the expansible member 14 is its natural, unconstrained free state. Deployment of the expansible member 14 requires that a member 16 be pulled proximally, as denoted by arrow 9 in FIGS. 3A and 4A. FIG. 3A illustrates a malecot member 14 in its natural retracted state and FIG. 3B shows this expansible member 14 in its expanded state at a distal end 12B of the catheter 11. FIG. 4A illustrates another embodiment that comprises a tubular braided mesh member 14 in its free retracted state at a distal end 12C of the catheter. FIG. 4B illustrates this expansible member 14 in its deployed expanded configuration. The manner in which these expansible members 14 may be assembled onto the catheter 11 and the way in which these members 14 may interact with other components of the device 10 are similar.

Referring back to FIG. 1, a proximal end of expansible member 14 is connected to the distal end 12 of tubular member 11 at connection point 15. The connection may be made with a crimp process, use of shrink tubing such as polyester tubing, adhesives such as glue, heat staking member 14 into member 11, or a combination thereof. A distal end of expansible member 14 is connected to the push/pull member 16 at connection point 17. Push/pull member 16 may be formed from metals (e.g., stainless steel or NITINOL®) or from polymer materials such as nylon, polyurethane, polyimide, PEEK®, PEBAX®, and the like. Member 16 has a diameter small enough to go through the tubular member 11 and a length that is long enough to traverse the length of the tubular member 11. The proximal end 13 of members 11 and 16 incorporate a handle assembly 18. A first part of the handle 19 is connected to the proximal end 13 of member 11. A second part of the handle 20 is connected to proximal end of member 16. Handle parts 19 and 20 provide for an enhanced grip on members 11 and 16, allowing the user to more conveniently move these members with respect to each other for the purpose of deploying and retracting the expansible member 14. Moving parts 19 and 20 away from each other causes the deployment of expansible member 14 and moving them towards each other causes the retraction of expansible member 14.

Figures 5A, 5B, 5C:
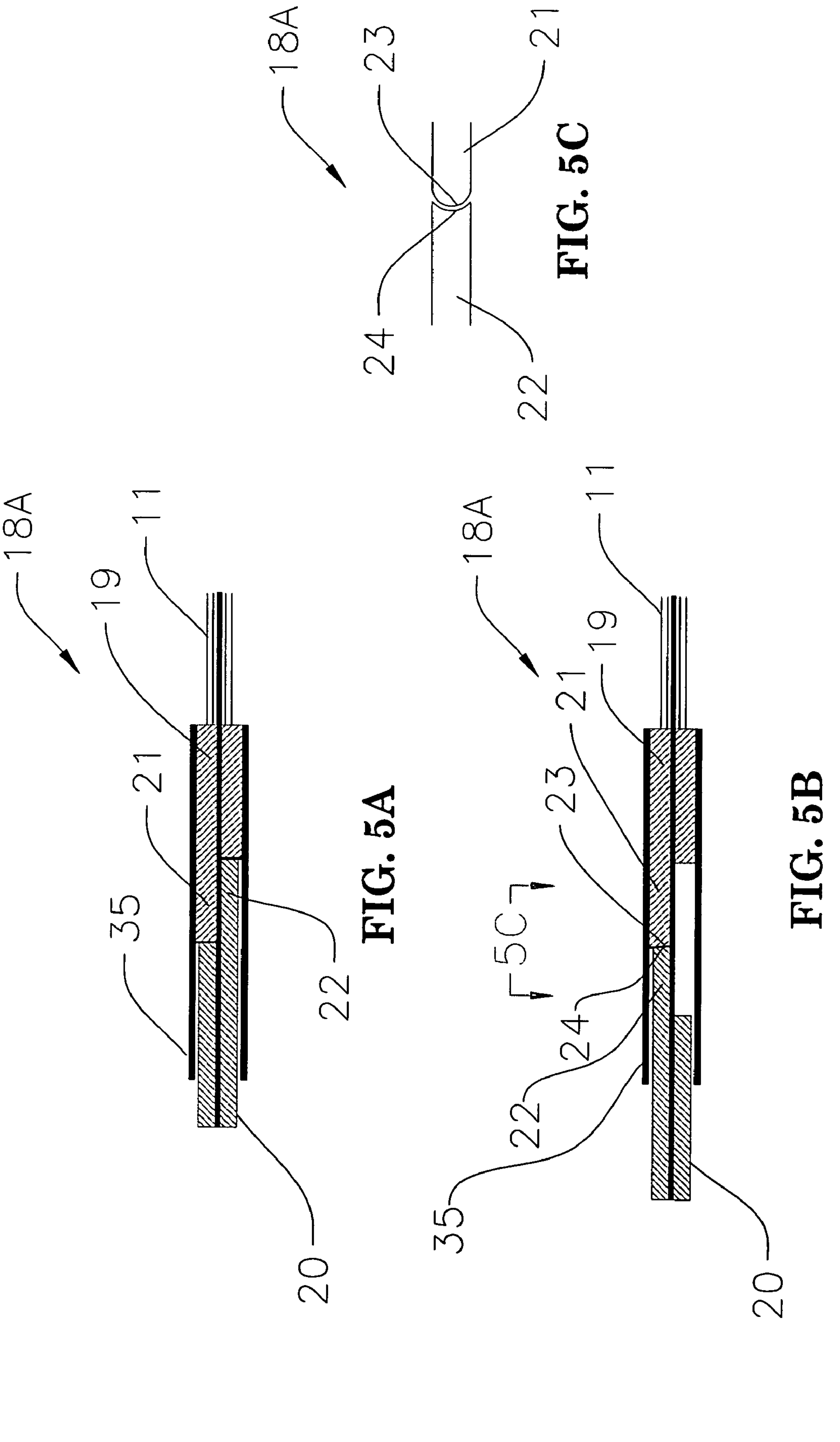
FIGS. 5A through 5C illustrate an alternative embodiment of the deployment means that may be employed in any of the device disclosed herein.

Referring now to FIGS. 5A through 5C, if no friction is built into the movement of members 11 and 16, handle assembly 18A may be designed to allow the deployed state of expansible member 14 to be held in position. This is because the lack of friction allows members 11 and 16 to move freely with respect to each other forcing the expansible member 14 back to its natural retracted state. Hence, locking features 21 and 22 of handle parts 19 and 20 respectively may be locked to maintain the expansible member 14 in a deployed configuration. In operation, parts 19 and 20 are moved apart until features 21 and 22 completely slide over each other. Handle part 20 can then be twisted with respect to part 19 by approximately 180° degrees, allowing the proximal end 21 of handle part 19 to rest over the distal end 22 of handle part 20, as shown in FIG. 5B. These ends 21 and 22 may be serrated or one end may have a half circular protrusion, as in feature 23 on proximal end of part 19, and the other end have a half circular indentation, such as feature 24 on the distal end of part 20, allowing these ends to detent into each other. A top view of this locking mechanism is illustrated in FIG. 5C showing the handle assembly in a deployed position. This locking mechanism may be beneficial to greatly reduce the chances of parts 19 and 20 slipping relative to each other causing unintended retraction. To further secure and stabilize the handle assembly 18A, particularly during deployment of expansible member 14, a handle housing 35 may at least be partially disposed over parts 19 or 20. In FIG. 5A, housing member 35 is attached to the first part of the handle 19 and is long enough that when member 14 is deployed and features 23 and 24 are in contact, member 35 extends proximally beyond feature 22.

Figure 6:
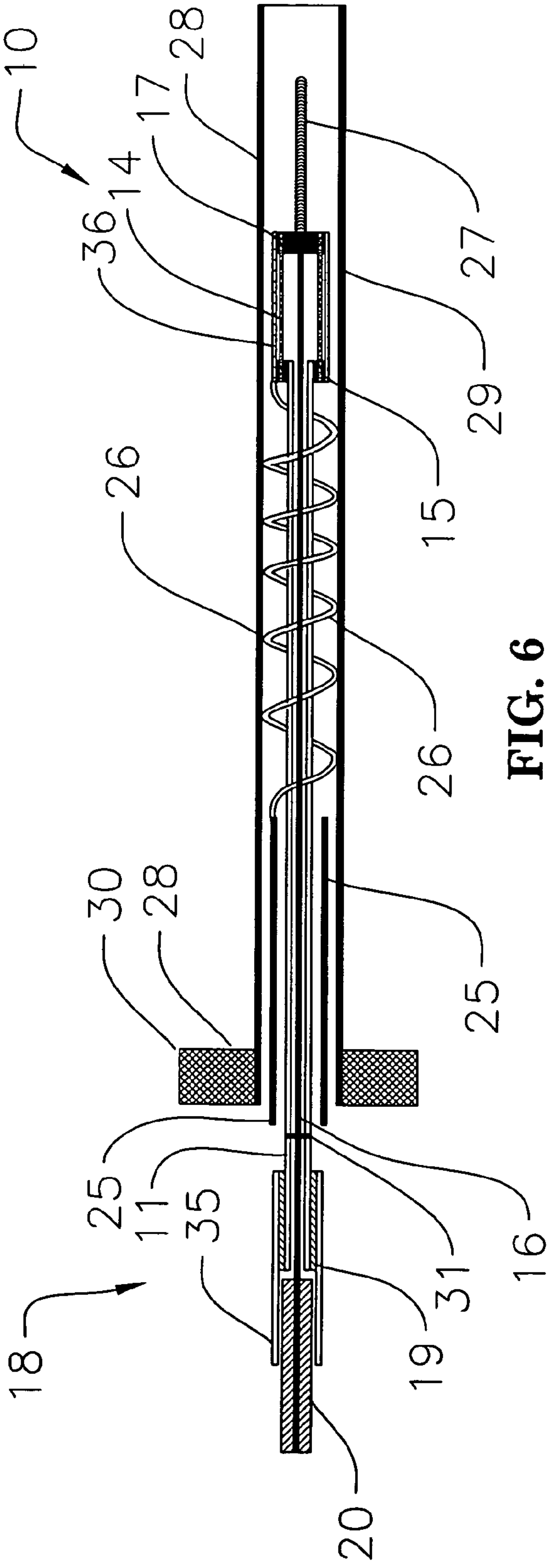
FIG. 6 illustrates a system for hemostasis of a puncture site in a body lumen employing the device of FIG. 1 in conjunction with a loading element.
Figure 7:
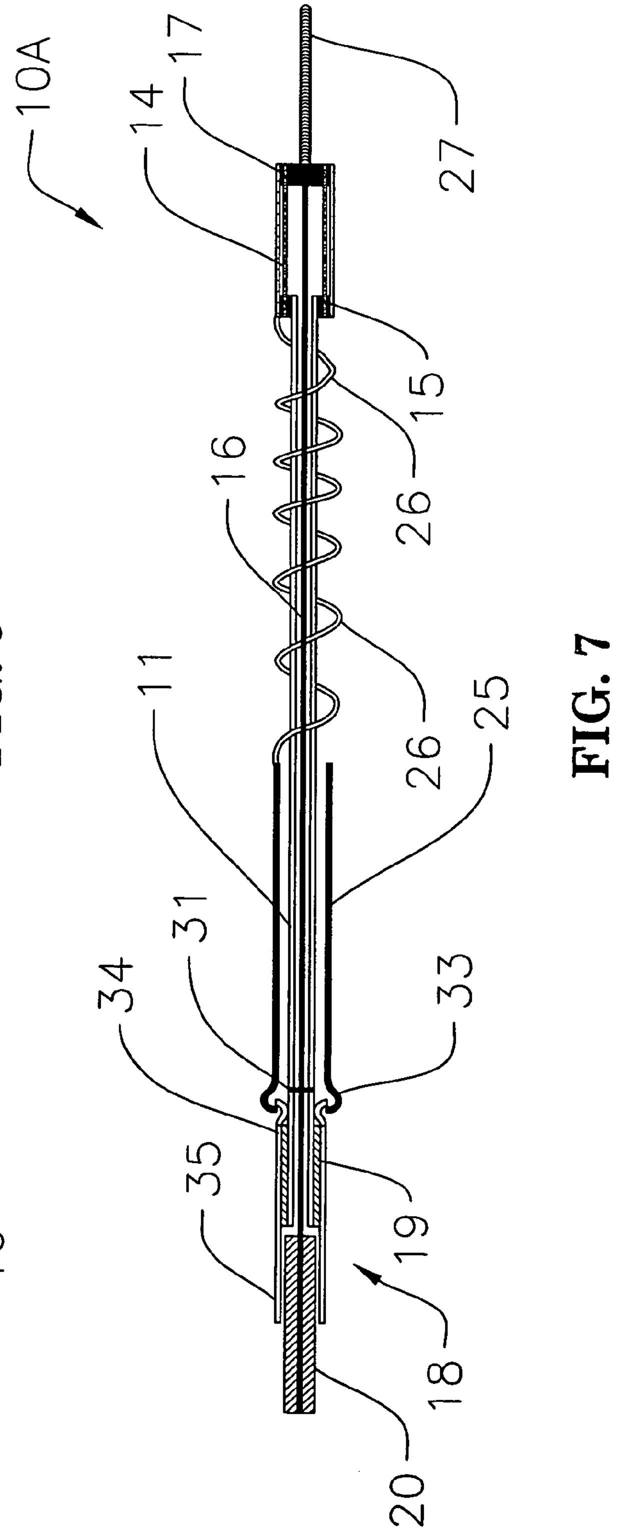
FIG. 7 illustrates another device for hemostasis of a puncture site in a body lumen employing a locking mechanism.

Referring now to FIGS. 1, 6, and 7, device 10 also includes a second flexible tubular member 25 that is slidably disposed over the first tubular member 11. Second member 25 is formed from a variety of medical grade materials, including polymer materials such as nylon, polyurethane, polyimide, PEEK®, PEBAX®, and the like. Second member 25 is shorter than first member 11 and may have a length in range from about 5 cm to about 40 cm, preferably in the range from about 10 cm to about 20 cm. A distal end of member 25 is connected to the tension coil spring 26. Tension coil spring 26 encompasses first member 11, wherein its distal end is connected to member 11 proximal the expansible member 14 at connection point 15.

Tensioning member 26 may be formed from a variety of medical grade materials, including suitable metals such as stainless steel or preferably shape memory or superelastic metals such as NITINOL®. The amount of force that expansible member 14 can exert against a vessel wall at the puncture site primarily depends on the diameter of the wire used, the diameter of the resulting coil, the pitch of the coil, and/or the total number of the loops in the coil of the tensioning member 26. The number of loops in the coil spring 26 may be in the range from about 1 loop to about 30 loops, preferably in the range from about 3 loops to about 20 loops. The coils are preferably wound tightly with little or no pitch between the loops when the coil 26 is at its relaxed state. The wire diameter used to fabricate the coil 26 may be in the range from about 0.02 mm to about 1 mm, preferably in the range from about 0.05 mm to about 0.5 mm. The fabricated coil 26 may have a diameter in the range from about 1 mm to about 10 mm, preferably in the range from about 1.5 mm to about 5 mm in a relaxed state. The diameter of the tension coil spring 26 in the preferred embodiment of this invention is chosen to be greater than the inside diameter of a delivery sheath. For example, when a 5 Fr sheath is used the diameter of coil 26 would be greater than 1.75 mm. The greater this difference, the greater the interference between the coil spring 26 and the sheath, and consequently the greater is the resulting tension on the expansible member 14 against the vessel wall as the sheath is being removed. The operation of device 10 is described in greater detail below with respect to FIGS. 8A through 8D.

As shown in FIGS. 1, 6, and 7, the distal end 12 of device 10 may include a tip deflector 27. Deflector 27 prevents element 17 from damaging the vessel wall on the opposite side of the puncture site. This may happen if the user excessively compresses the skin at or adjacent to the puncture site, which potentially could happen when the device 10 is being removed. Deflector 27 may be formed from a variety of medical grade materials, including flexible metal coil materials or polymer materials such as nylon, polyurethane, polyimide, PEEK®, PEBAX®, and the like. In one embodiment, deflector 27 may be formed from a small diameter wire, possibly the extension of member 16, coated with a soft polymer material. Deflector 27 will generally have a diameter equal to or smaller than the catheter diameter at element 17 and a length in the range from about 1 cm to about 10 cm, preferably from about 2 cm to about 4 cm. A welding process may be utilized to provide for a short and strong connection point at element 17. It will be appreciated however that the need for a deflector tip 27 may be alleviated if element 17 itself is made short and blunt.

Referring now to FIG. 6, device 10 may be equipped with a catheter loading element 28 when tensioning member 26 at its relaxed state is larger than the inner diameter of the delivery sheath in order to facilitate insertion of the device 10 through the sheath. Loading element 28 generally comprises an elongated tubular member 29. An outer diameter of member 29 is smaller than the opening in a hub of the sheath and can penetrate a seal in the sheath. An inner diameter of loader 28 is large enough to allow the catheter 11 to completely slide through. Loader 28 has a length long enough to at least contain all the elements of the catheter 11 distal to and including the tensioning member 26. Loader 28 may include a feature 30 at a proximal end. This feature 30 may be used as a stop against the hub of the introducer sheath, preventing the loading element 28 from completely sliding into a lumen of the sheath. Loading element 28 may be formed from coiled stainless steel tubing or polymer materials such as nylon, polyurethane, polyimide, PEEK®, PEBAX®, and the like.

Referring now to FIG. 7, introduction of the device 10A into the sheath and removal of the device 10A from the body may also be facilitated by incorporating a locking mechanism 33 at a proximal end of second tubular member 25 that may be interlocked with a feature 34 on a distal end of handle 19. The locking mechanism 33, 34 allows tensioning member 26 to be maintained in a stretched state so as to reduce the coil diameter to below that of the inner diameter of the delivery sheath and thereby allowing the device 10A to slide through the sheath without interference. In other embodiments, locking features on the catheter 11 may interlock with the locking mechanism 33 on member 25. Even when member 25 is equipped with an interlocking mechanism 33 so that tensioning member 26 does not interfere with the sheath, loader 28 may still provide for enhanced introduction of the device 10A into the sheath.

As shown in FIGS. 1, 6, and 7, tubular member 11 has a visual mark 31. When device 10 is inserted through the delivery sheath, alignment of mark 31 with the opening of the hub of the sheath indicates that catheter 10 has been advanced enough through the sheath to expose the expansible member 14 in the lumen of the vessel. Alternatively, when element 30 of loading element 28 is against the hub of the sheath, alignment of mark 31 with the proximal end of feature 30 may indicate appropriate advancement of the expansible member 14 in the vessel lumen. Optionally, alignment of the distal end of handle 19 with the hub of the sheath or loading element 30 may eliminate the need for mark 31. Still further, mechanical means may be utilized for proper location of the expansible member 14 within the lumen of the vessel.

Figure 8B:
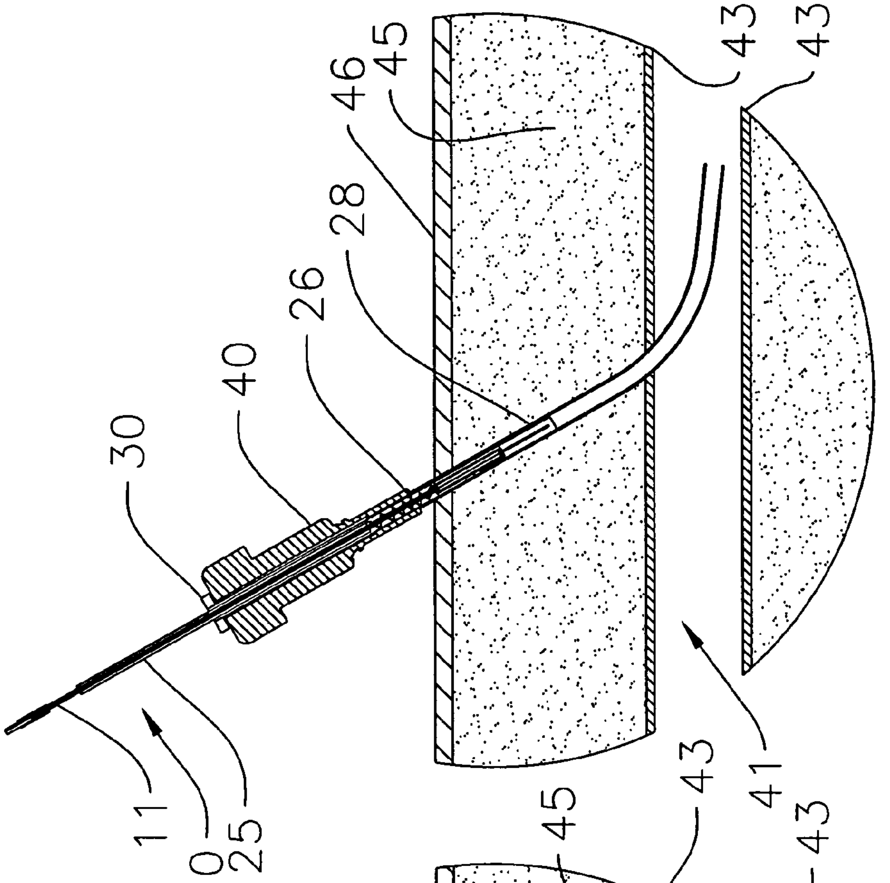
FIGS. 8A though 8D illustrate a method for hemostasis of a puncture site in a body lumen employing the device of FIG. 1.
Figure 8A:
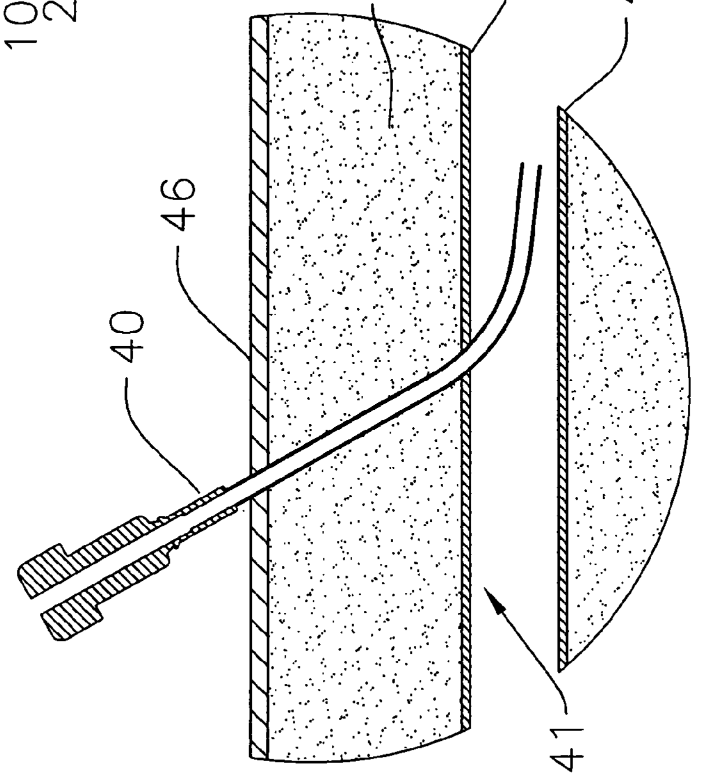
Figure 8D:
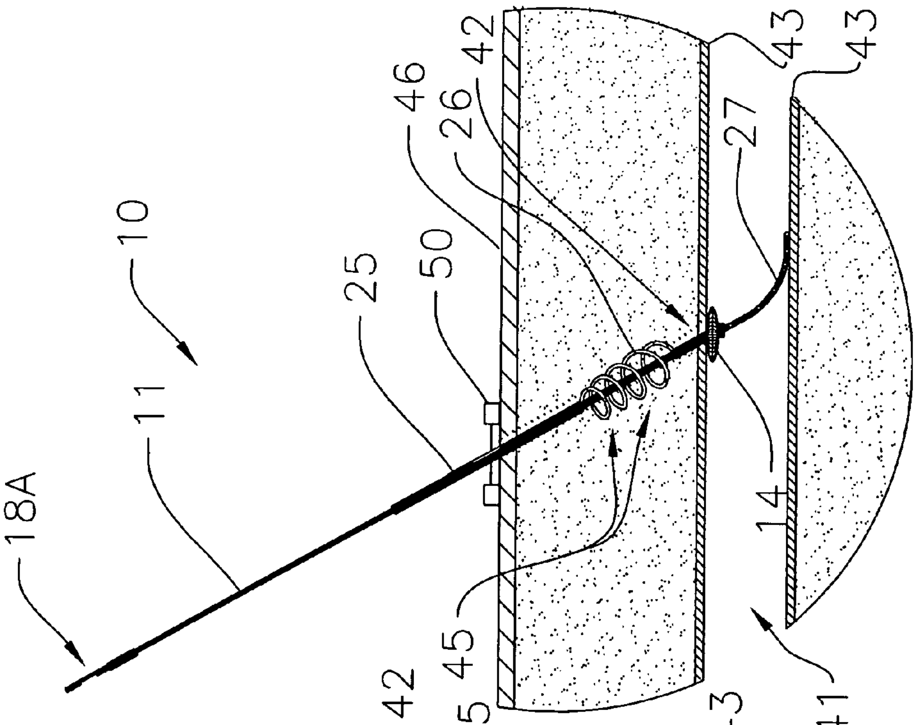
Figure 8C:
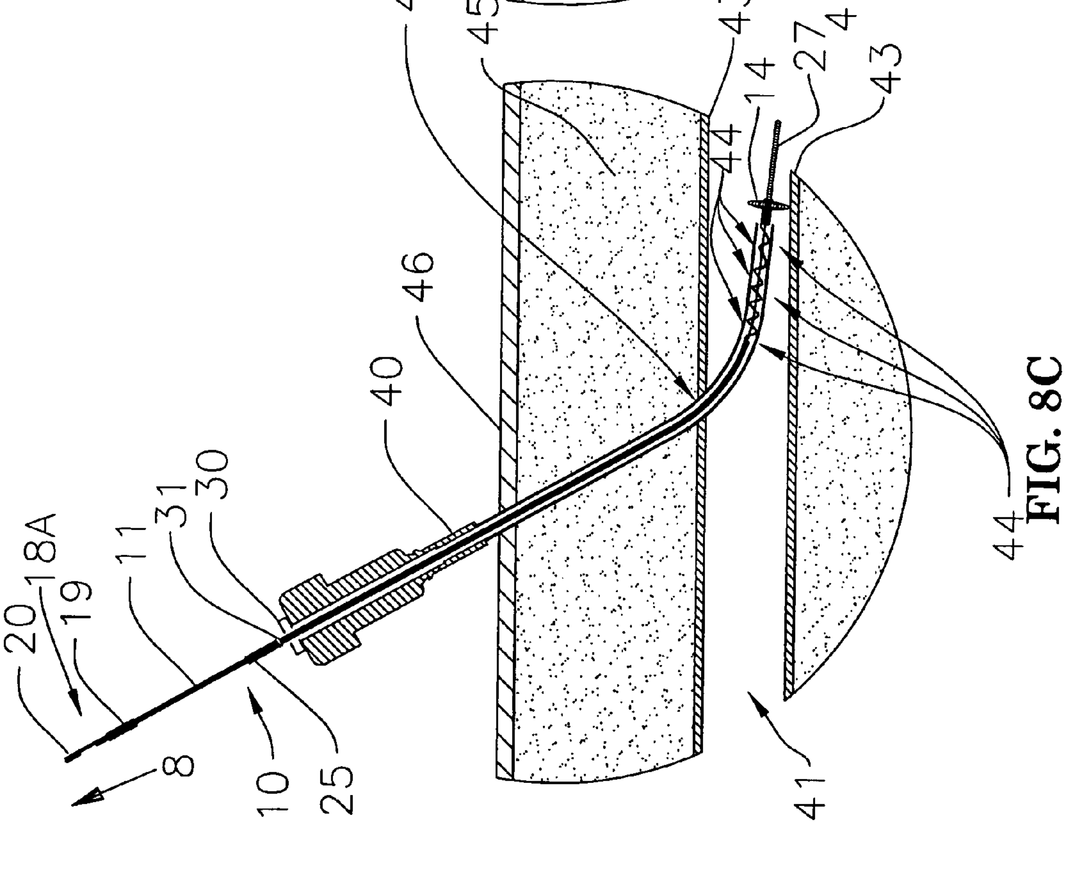

Referring now to FIGS. 8A through 8D, a method for hemostasis of a puncture site in a body lumen employing the device of FIG. 1 is illustrated. FIG. 8A depicts an existing delivery sheath 40 through an opening in a skin surface 46, tissue tract in fascia 45, and vessel wall 43 and seated in a vessel lumen 41 at the completion of an interventional procedure. Device 10 including loading element 28 is then inserted through the hub of the sheath 40 so that loading element 28 at least penetrates the seal of sheath 40 or until feature 30 is against the hub of the sheath 40, as shown in FIG. 8B. Loader 28 may now be removed. Alternatively, device 10 with loader 28 present can be pushed into sheath 40 until the identifying mark 31 on member 11 is aligned with feature 30 of loading element 28. As shown in FIG. 8C, expansible member 14 is then deployed by holding part 19 of handle assembly 18A stationary and moving member 20 proximally, as depicted by arrow 8 and described in detail with respect to FIGS. 5A through 5C. Second tubular member 25 may then be pulled proximally until resistance is felt indicating that expansible member 14 is at the distal end of sheath 40. If member 25 is equipped with a locking mechanism 33 in a locked position, member 11 or the handle assembly 18A may be grasped to pull the device 10 proximally and seat member 14 against the tip of the sheath 40. Member 25 is then unlocked at this point. Optionally, the sheath 40 at the hub may be gently removed from the body so as to seat the expansible member 14. There may be a short time period of nominal bleeding from when the distal end of the sheath 40 is removed from the vessel lumen 41 and when the expansible member 14 is set against the puncture site 42.

Referring again to FIG. 8C, once the distal end of sheath 40 exits the vessel wall 43 at puncture site 42 and the expansible member 14 is placed against the vessel wall 43 at the puncture site 42, the resistance offered by member 14 against the vessel wall 43 will cause catheter 10 to exit the sheath 40. The amount of interference between tensioning coil 26 and sheath 40 at points 44 determines the amount of force exerted by member 14 against the vessel wall 43. Overcoming the friction force between the fascia 45 and the outer surface of sheath 40 as well as between the tensioning coil 26 and the sheath 40 at points 44, sheath 40 is removed from the body exposing the loops of the coil 26 and lodging them into the fascia 45 one loop at a time. Loader 28 along with sheath 40 are removed and may be discarded.

Referring now to FIG. 8D, the interference between the loops of the coil 26 and fascia 45 provides the hold and retains expansible member 14 under tension against the vessel wall 43 at the puncture site 42. The tension applied to the expansible member 14 is sufficient for complete hemostasis, typically in a range from about 0.5 ounce to 30 ounces. When the sheath 40 and/or loader 28 are removed and the coil 26 gets embedded in the tissue 45, the amount of the tension at the puncture site 42 may drop as the coil 26 recoils some to engage itself in the tissue 45. The amount in the reduction of tension is dependant on the tissue type 45 surrounding the puncture site 42, the nature of the coil spring 26, and the thickness of the fascia 45. These factors have been considered in the proper design of the coil 26 of the present invention.

If greater tension is desired once the device 10 is first seated, second tubular member 25 may be moved proximally and released increasing the amount of compression that expansible member 14 applies on the vessel wall 43. The increase in the pull force may be limited by the amount of proximal movement of member 25, which can be determined by the proper length of member 25 and the distance between the proximal end of member 25 and distal end of handle part 19. The pull force may be limited by interference of members 25 and 19. The pull force may also be limited by interference between the coil 26 and the first tubular member 11. In particular, the closer the diameter of member 11 to the inside diameter of coil 26, the less stretch member 26 can experience before the coil diameter is reduced enough to interfere with member 11. In the above methodologies, when second member 25 stops moving respect to first member 11, that may be an indication that the maximum allowable and safe pull force has been reached.

Device 10 remains in the body for an adequate period of time. Occlusive compression may be applied proximal to the puncture site 42 when the device 10 is to be removed. Expansible member 14 is retracted by manipulation of handle assembly 18A and member 25 is grasped so as to pull the device 10 out of the body. Pulling on member 25 causes coil 26 to stretch, reducing the coil diameter, and consequently reducing the amount of interference between coil 26 and fascia 45. If device 10 is equipped with locking features 33 and 34, removal of device 10 may be accomplished by first pulling on member 25 proximally and interlocking features 33 and 34. This easily disengages device 10 from the fascia 45. Removal of the device 10 may be followed by a few minutes of manual compression at the skin surface 46 to achieve complete hemostasis.

As shown in FIG. 8D, device 10 may include an external clip 50. Clip 50 couples member 25 and rests on the patient's skin surface 46. Clip 50 may be used as a safety feature to further secure and keep expansible member 14 under tension. It may also be used when greater tension is desired than that provided by interaction of coil 26 with sheath 40 and fascia 45 alone. In another embodiment (not shown), coil member 26 may be intended to function only as a tensioning member. Coil 26 in this embodiment may have a diameter smaller than the inner diameter of the sheath 40 and be formed from elastomeric material. This elastomeric member is preferably in a form of a tube which is attached to the first member 11 at point 15 and to the distal end of second member 25. Once the device 10 is placed in the sheath 40, and expansible member 14 is deployed, member 25 is used to place expansible member 14 against the vessel wall 43 at the puncture site 42 and to apply the required tension to the device 10. The substantial hold once the tension is applied is then provided by external means, such as the external clip 50. This device 10 may have the advantage of being easier to load and insert through the sheath 40 as the external clip 50 provides anchoring.

Figures 9A, 9B, 9C:
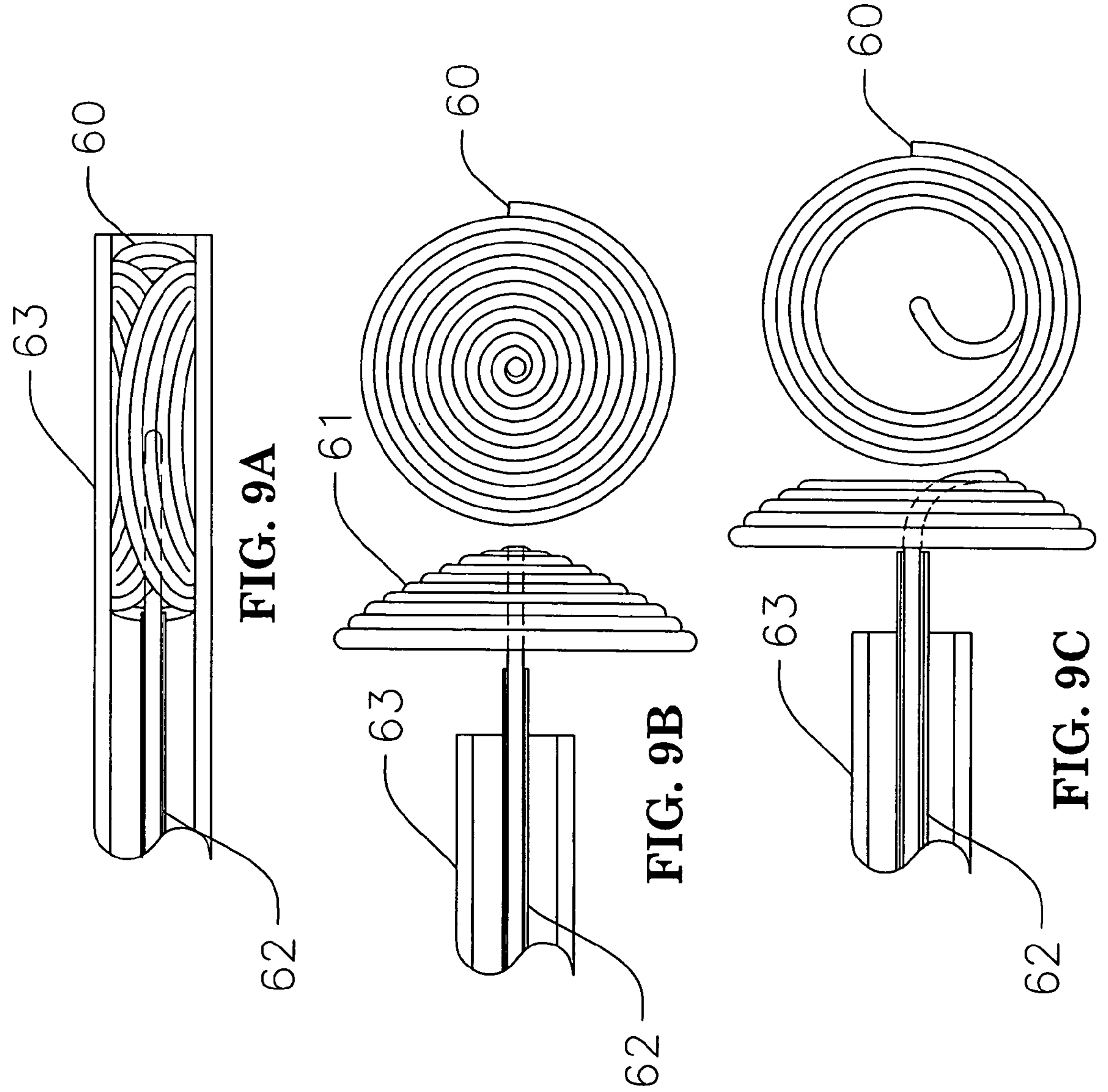
FIGS. 9A through 9C illustrate another embodiment of the expansible member in a retracted configuration, expanded configuration, and retraction through unwinding process, respectively that may be employed in any of the devices disclosed herein.

Referring now to FIGS. 9A through 9C, a still further embodiment of the expansible member 60 of the present invention is illustrated. The expansible member 60 preferably comprises coiled string constructed from small diameter tubing that is flexible. The tubular configuration may have a suture or small diameter wire in its lumen to add to its tensile strength. Flexible member 60 may be formed from medical grade materials, including polymer materials such as nylon, polyurethane, polyimide, PEEK®, PEBAX®, and the like. Flexible member 60 can be coiled into an expanded configuration comprising a disc or dome shape 61. Adjacent loops of member 60 may be adhered lightly through a heating or a gluing process. Member 60 at the center is fed through a tube 62, wrapped around tube 62, and is housed in a tubular member 63, as shown in FIG. 9A. To deploy the expansible member 60, tube 62 is pushed forward to expose the expansible member 61. Once extracted from tubular member 63, the expansible member 61 unfolds into a disc or a dome configuration as illustrated in FIG. 9B. The sealing process is attained by pulling on tube 62, allowing the expansible member 61 to press against the puncture site. Retraction is effected by pulling coil 60 through tube 62, causing the loops of the expansible member 61 to unwind as depicted by FIG. 9C. Still further embodiments of such an expansible member are disclosed in U.S. Patent Application No. 2003/0120291, which describes a temporary seal and method for facilitating anastomosis and is also incorporated herein by reference.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A device for hemostasis of a puncture site at the end of a tissue tract leading to a body lumen, the device comprising:

a first tubular member having a proximal end and a distal end configured for insertion through an existing sheath so as to traverse a length of the sheath;

a second tubular member slidably disposed over the first tubular member and configured for insertion through the existing sheath so as to traverse the length of the sheath;

an expansible member disposed on the distal end of the first tubular member and configured to be expandable within a lumen of a vessel and to be seated against the puncture site when expanded; and a spring coil tensioning member slidably disposed over the first tubular member, a proximal end of the tensioning member being fixedly attached to a distal end of the second tubular member and a distal end of the tensioning member being fixedly attached to a distal portion of the first tubular member; and wherein the spring coil tensioning member has a lengthened configuration when tension is applied by the second tubular member and a compressed configuration in the absence of such tension and, when in the compressed configuration, is capable of embedding in subcutaneous tissue of the tract leading to the vessel so as to anchor and maintain tension of the expansible member against the puncture site at a vascular surface of the lumen.

2. A device as in claim 1, wherein the spring coil is formed from wire having a diameter in a range from about 0.02 mm to about 1 mm.

3. A device as in claim 2, wherein the spring coil has from 1 to 30 loops.

4. A device as in claim 3, wherein the spring coil has a diameter in a range from about 1 mm to about 10 mm.

5. A device as in claim 1, wherein the spring coil tensioning member comprises stainless steel, shape memory alloy, or superelastic metal.

6. A device as in claim 1, wherein the expansible member comprises a braided filament, mesh layer, spring, coil, slotted tube, coiled string, or balloon.

7. A device as in claim 6, wherein the expansible member comprises a braided filament having small pores.

8. A device of claim 7, wherein the braided filament is coated with a hydrophobic coating.

9. A device as in claim 6, wherein the expansible member comprises coiled string having a disc or dome shape in an expanded configuration.

10. A device as in claim 6, further comprising a deformable membrane at least partially disposed over the expansible member.

11. A device as in claim 10, further comprising a membrane tip.

12. A device as in claim 1, further comprising a tip deflector coupleable to the first tubular member and distal the expansible member.

13. A device as in claim 1, further comprising expansible member deployment means coupleable to the proximal end of the first tubular member.

14. A device as in claim 13, further comprising a locking mechanism on the deployment means or second tubular member.

* * * * *